United States Patent [19]

Hakamatsuka et al.

[11] Patent Number: 5,135,394
[45] Date of Patent: Aug. 4, 1992

[54] EXTRACTION CAVITY FILLING MEMBER AND A MANUFACTURING METHOD THEREOF

[75] Inventors: Yasuharu Hakamatsuka; Hiroyuki Irie; Hiroshi Fukuda, all of Hachioji, Japan

[73] Assignee: Olympus Optical Co., Ltd., Tokyo, Japan

[21] Appl. No.: 754,358

[22] Filed: Aug. 29, 1991

Related U.S. Application Data

[63] Continuation of Ser. No. 457,321, Dec. 27, 1989, abandoned.

[30] Foreign Application Priority Data

Jan. 6, 1989 [JP] Japan ............... 64-935
Jan. 6, 1989 [JP] Japan ............... 64-936
Jan. 6, 1989 [JP] Japan ............... 64-937

[51] Int. Cl.⁵ .............................. A61C 8/00
[52] U.S. Cl. ..................... 433/173; 433/222.1
[58] Field of Search ........... 433/173, 174, 175, 176, 433/222.1

[56] References Cited

U.S. PATENT DOCUMENTS

| | | | |
|---|---|---|---|
| 3,849,887 | 11/1974 | Brainin | 433/173 |
| 4,293,302 | 10/1981 | Hassler et al. | 433/173 |
| 4,492,577 | 1/1985 | Farris et al. | 433/173 |
| 4,531,916 | 7/1985 | Scantlebury et al. | 433/176 |
| 4,673,355 | 6/1987 | Farris et al. | 433/222.1 |
| 4,854,873 | 8/1989 | Linden | 433/173 |
| 4,904,187 | 2/1990 | Zingheim | 433/173 |
| 4,915,628 | 4/1990 | Linkow et al. | 433/173 |
| 4,957,437 | 9/1990 | Shimura et al. | 433/174 |
| 4,957,819 | 9/1990 | Kawahara et al. | 433/173 |
| 4,960,381 | 10/1990 | Niznick | 433/173 |

Primary Examiner—Paul J. Hirsch
Attorney, Agent, or Firm—Frishauf, Holtz, Goodman & Woodward

[57] ABSTRACT

A ceramic member for a living body includes a first end portion formed of a material having affinity with a living body and consisting of a dense material, and a second end portion formed of a material having affinity with a living body and consisting of a porous material. A method of manufacturing a ceramic member for a living body, includes the steps of mixing a ceramic powder having affinity with a living body, water, and a binder to prepare a dense material slurry, mixing a ceramic powder having affinity with a living body, water, a binder, and a foaming agent to prepare a porous material slurry, injecting; in order to form a two-layered base material consisting of the dense material slurry and the porous material slurry, the dense material slurry and the porous material slurry obtained in the two steps in a mold such that the dense and porous material slurries are not mixed with each other, and drying the base material, and after the drying step, heating the base material at a predetermined rate, and sintering the base material at a predetermined temperature.

9 Claims, 2 Drawing Sheets

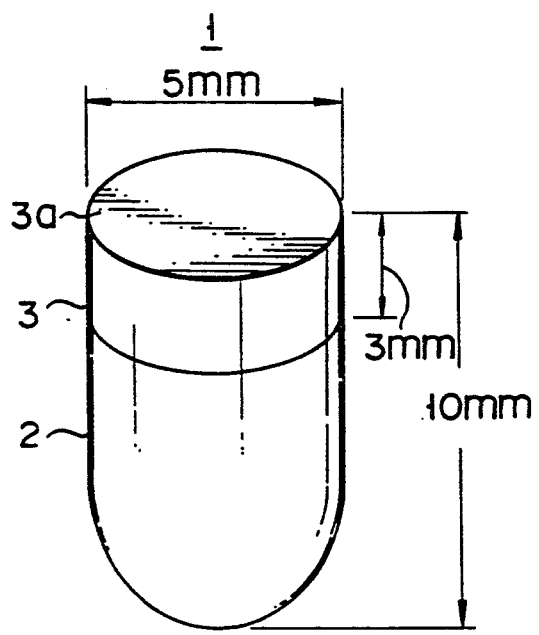
F I G. 1
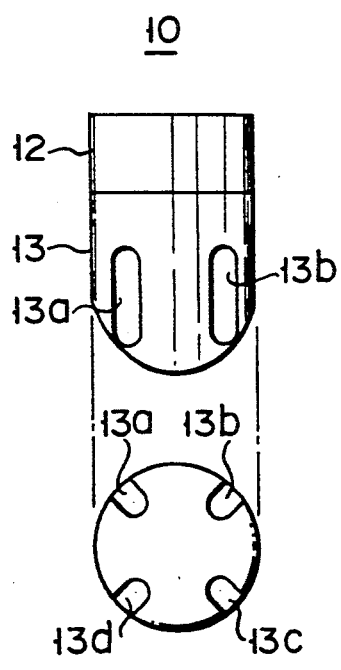
F I G. 2
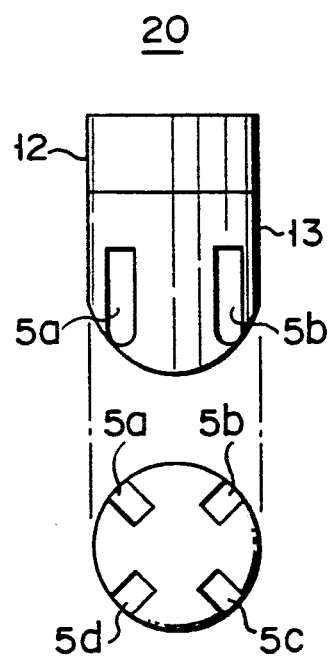
F I G. 3
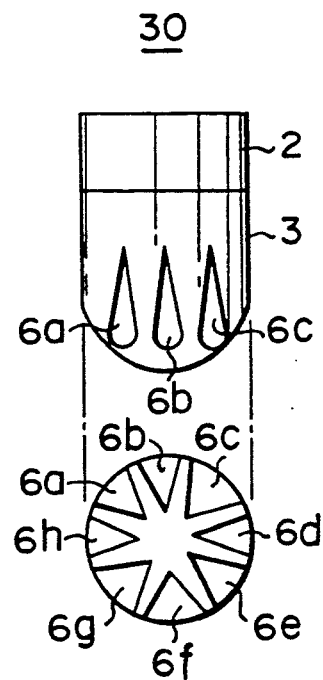
F I G. 4

EXTRACTION CAVITY FILLING MEMBER AND A MANUFACTURING METHOD THEREOF

This application is a continuation of application Ser. No. 07/457,321, filed Dec. 27, 1989, now abandoned.

BACKGROUND OF THE INVENTION

1. Field of the Invention

The present invention relates to a ceramic member for a living body which can be used as an extraction cavity filling material and a method of manufacturing the same.

2. Description of the Related Art

Recently, a ceramic member for a living body using a ceramic material having affinity with a living body has been manufactured. An example of the ceramic member for a living body is a filling material for a bone deficient portion. Examples of such a ceramic member are a dense material, a porous material, and a granule. A member for a living body consisting of a dense material has high strength and is resistant to infection since bacteria hardly enter into the member. A member for a living body consisting of a porous material or a granule can easily provide a good bonding state with a bone since it allows easy formation of a bone tissue in pores or gap portions of the member.

Therefore, ceramic members for a living body having the above properties are conventionally used as, e.g., an extraction cavity filling material. A ceramic member for a living body will be described below by taking an extraction cavity filling material as an example. The extraction cavity filling material is a filling material for preventing bone absorption and alveolar ridge lowering in an extraction cavity produced after tooth extraction. An extraction cavity filling material consisting of a ceramic material having affinity with a living body generally has a structure in which the dense material or a single-crystal material is used in a core portion and a porous material is coated on the surface of the core portion. With such a structure, the strength as a root and the affinity with a bone tissue are obtained.

An example of such an extraction cavity filling material is proposed in Published Unexamined Japanese Patent Application No. 61-50558. This extraction cavity filling material is obtained by molding a calcium phosphate compound consisting of a porous or dense material into a truncated cone or a circular pillar. Alveolar ridge lowering after tooth extraction can be prevented by transplanting an extraction cavity filling material having such a shape in an extraction cavity.

Ceramic members for a living body obtained by conventional manufacturing methods, however, are sometimes not firmly bonded to a bone tissue or cause infection with high possibility. For example, when a porous material is used as an extraction cavity filling material, bacteria easily enter into small pores formed in the surface of the material. Therefore, a gum portion which is in contact with the material is infected.

When a granule is used as an extraction cavity filling material, the material may be dislodged by an internal pressure or the like if another tooth is lost to lower an alveolar ridge.

In addition, when a dense material is used as an extraction cavity filling material, the material is not firmly bonded to a bone material since the bone tissue is not formed in the dense material.

Furthermore, in order to form an artificial root in an extraction portion, a root post must be transplanted in an extraction cavity filling material. Since, however, conventional extraction cavity filling materials do not have a function as an artificial root receiving member, an artificial root cannot be formed.

SUMMARY OF THE INVENTION

It is an object of the present invention to provide a ceramic member for a living body which can be firmly bonded to a bone tissue, which does not cause infection due to bacteria, and which has good affinity with a living body, and a method of manufacturing the same.

The ceramic member according to the present invention is formed of a material having affinity with a living body and has a first end portion consisting of a dense material and a second end portion consisting of a porous material.

When the ceramic member for a living body according to the present invention is used as an extraction cavity filling member, the first end portion is brought into contact with a bone tissue of an extraction cavity, and the second end portion is brought into contact with a gum portion. Therefore, bacteria are prevented from entering into the extraction cavity filling member, and the first end portion can be firmly bonded to the bone tissue.

In addition, in a method of manufacturing a ceramic member for a living body according to the present invention, a ceramic powder having affinity with a living body, water, and a binder are mixed to prepare a dense material slurry. In addition, a ceramic powder having affinity with a living body, water, a binder, and a foaming agent are mixed to prepare a porous material slurry. The two types of slurries obtained in the above two steps are injected and dried in a predetermined mold such that they are not mixed with each other and formed two layers, thereby obtaining a base material. Thereafter, the base material is heated at a predetermined rate and sintered at a predetermined temperature.

BRIEF DESCRIPTION OF THE DRAWINGS

FIG. 1 is a perspective view showing an extraction cavity filling member according to the first and third embodiments;

FIG. 2 is a view showing an extraction cavity filling member in which semi-circular pillar-like recess portions are formed in a bone bonding portion;

FIG. 3 is a view showing an extraction cavity filling member in which square-pillar-like recess portions are formed in a bone bonding portion;

FIG. 4 is a view showing an extraction cavity filling member in which triangular pyramidal recess portions are formed in a bone bonding portion;

DETAILED DESCRIPTION OF THE PREFERRED EMBODIMENTS

1st Embodiment

Figures 5, 6:
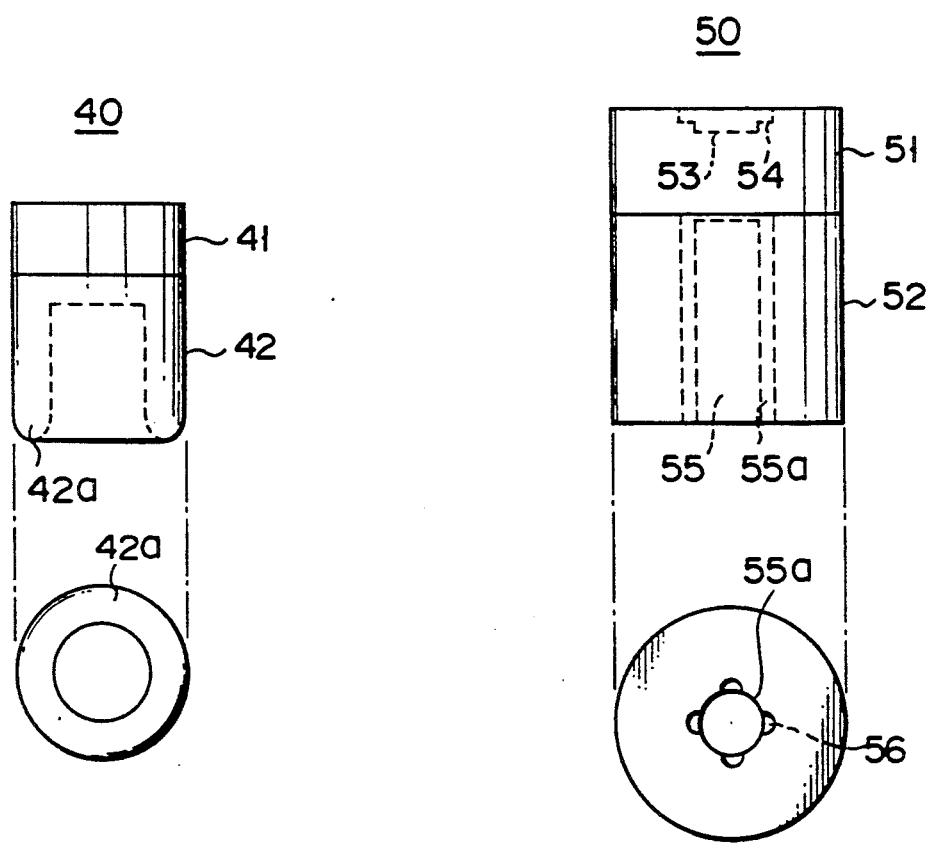
FIG. 5 is a view showing a comparative extraction cavity filling member.
FIG. 6 is a view showing an extraction cavity filling member according to the fifth embodiment.

According to the first embodiment, $\beta$-tricalcium phosphate ($\beta$-TCP) is used as a ceramic powder having affinity with a living body to form an extraction cavity filling material. First, a material powder serving as a ceramic powder having affinity with a living body is formed as follows. That is, calcium carbonate $CaCO_3$ and calcium hydrogen phosphate dihydrate are used to adjust a Ca/P molar ratio to be 1.50, and a $\beta$-TCP powder as a material powder is synthesized by a mechanochemical reaction. The synthesized material powder is heat-treated at 900° C. In this heat treatment, particles of the material powder can be stabilized to prevent crazing during drying of a slurry and shrinkage upon final sintering as will be described later.

6 ml of a polyacrylic ammonium salt-based deflocculating agent and 12 ml of pure water are added to 30 g of the above material powder, and the resultant material is sufficiently mixed to prepare a homogeneous slurry. 2.7 ml of a foaming agent consisting of 10 mol of a mixture a polyoxyethylene nonylphenyl ether and an ethylene oxide are added to the slurry, and the resultant material is mixed and foamed in a mixer, thereby obtaining a porous material slurry. This porous material slurry is sintered in the subsequent step to obtain a porous material.

10 ml of a 10% polyacrylic ammonium salt solution are added to 20 g of the above material powder, and the resultant material is sufficiently mixed to prepare a homogeneous slurry. In this manner, a dense material slurry is prepared. This dense material slurry is sintered in the subsequent step to obtain a dense material.

The above porous material slurry and the dense material slurry are injected in a mold in this order and dried. This mold is obtained by covering the inner surface of a magnetic vessel with paraffin paper. The and then the dense material slurry is injected in the mold so as not to be mixed with the porous slurry. Note that since the porous material slurry and the dense material slurry have predetermined viscosities, they are not mixed with each other like liquids. In this manner, two layers constituted by the porous and dense material slurries are formed in the mold. The two layers are dried at room temperature and then sintered. Sintering is performed such that the material is kept at 350° C. for one hour, heated up to 1,100° C. at a heating rate of 100° C./hour, kept at 1,100° C. for one hour, and then cooled in the furnace.

In this manner, the porous and dense materials are firmly joined to form a two-layered joint member. Note that when this joint member is measured, the porosity of the porous member was about 50%, and its pore diameter was 100 $\mu$m.

The above joint member is cut into a desired shape to obtain an extraction cavity filling member. FIG. 1 is a perspective view showing the shape of the extraction cavity filling member obtained by cutting the joint member. In this extraction cavity filling member 1, a portion to be brought into contact with a bone tissue consists of a porous material 2, and a portion to be brought into contact with a gum portion consists of a dense material 3. The distal end of the porous material 2 is parabolic, and an upper surface 3a of the dense material 3 to be brought into contact with a gum epithelium is mirror-polished.

When the extraction cavity filling member 1 having the above structure is filled in an extraction cavity, the porous material 2 is brought into contact with a bone tissue. Therefore, the bone tissue easily enters into a large number of small pores formed in the material 2 to realize a good bonding state with the bone. In addition, the dense material 3 is brought into contact with a gum portion, and the upper surface 3a of the dense material 3 exposed to an atmosphere is mirrorpolished. Therefore, the gum portion can be reliably protected from infection.

According to the method of manufacturing an extraction cavity filling member of the first embodiment, the extraction cavity filling member 1 having good affinity with a living body, which can be firmly bonded to a bone tissue and can reliably prevent a gum portion from infection, can be obtained.

2nd Embodiment

According to the second embodiment, hydroxy apatite (HAP) is used as a ceramic powder having affinity with a living body to form an extraction cavity filling member. First, following the same procedures as in the first embodiment, a material powder consisting of hydroxy apatite is synthesized by a mechanochemical method. The synthesized material powder is heat-treated at 950° C. to stabilize particles of the material powder.

A porous material slurry and a dense material slurry are prepared as follows. That is, 6 ml of a polyacrylic ammonium salt-based deflocculating agent and 12 ml of pure water are added to 30 g of a hydroxy apatite powder, and the resultant material is sufficiently mixed to prepare a homogeneous slurry. 2.7 ml of a foaming agent consisting of 10 mol of a combination of polyoxyethylene nonylphenel ether and ethylene oxide are added to the slurry, and the resultant material is mixed and foamed in a mixer, thereby obtaining a porous material slurry. A dense material slurry is prepared by adding 10 ml of a 10% polyacrylic ammonium salt solution having functions as a binder and a deflocculating agent to 20 g of a hydroxy apatite powder and sufficiently mixing the resultant material to prepare a homogeneous slurry.

The porous material slurry is injected into a mold obtained by covering the inner surface of a magnetic vessel with paraffin paper. Thereafter, the dense material slurry is injected so as not to be mixed with the porous material slurry. In this manner, two layers constituted by the porous and dense material slurries are formed in the mold. The two layers are dried at room temperature and then sintered. Sintering is performed such that the material is kept at 350° C. for one hour, heated up to 1,200° C. at a heating rate of 100° C./hour, kept at 1,200° C. for one hour, and then cooled in the furnace.

In this manner, the porous and dense materials are firmly joined to obtain a two-layered joint member. Note that when this joint member was measured, the porosity of the porous material was about 50%, and its pore diameter was 100 to 300 $\mu$m.

The above joint member is cut to form a bullet-like extraction cavity filling member as shown in FIG. 1. An upper surface 3a of the dense material to be brought into contact with a gum portion is mirror-polished.

The above extraction cavity using hydroxy apatite can protect a gum portion against infection due to bacteria. Therefore, the porous material 2 can be firmly bonded to a bone tissue.

According to the second embodiment, therefore, an extraction cavity filling member having good affinity with a living body can be obtained as in the first embodiment.

In each of the above first and second embodiments, a method of manufacturing an extraction cavity filling member has been described. The present invention, however, is not limited to the above embodiments but can be applied to a method of manufacturing another type of a ceramic member for a living body.

3rd Embodiment

An extraction cavity filling member according to the third embodiment has a figure as shown in FIG. 1. This extraction cavity filling member is a joint member constituted by a dense material 3 consisting of a dense texture and a porous material 2 consisting of a porous texture. As described above, the extraction cavity filling member is circular-pillar-like as a whole and has a flat end face at the dense material 3 side and a parabolic end portion at the porous material 2 side. The diameter of the extraction cavity filling member is 5 mm, and its total length is 10 mm. Referring to FIG. 1, an upper 3-mm long portion is the dense material 3, and a lower 7-mm long portion is the porous material 2. Since the dimensions of the extraction cavity filling member are set as described above, the dense material 3 is brought into contact with a soft tissue such as a gum portion and the porous material 2 is brought into contact with a bone tissue upon extraction cavity filling. As described in the first embodiment, the dense material 3 consists of $\beta$-tricalcium phosphate, and the porous material 2 consists of porous $\beta$-tricalcium phosphate having a porosity of 50%. In addition, an upper surface 3a of the dense material 3 is mirrorpolished.

An experiment in which the extraction cavity filling member having the above arrangement was actually transplanted in an extraction cavity will be described below. A hole having a diameter of 5 mm and a depth of 10 mm was formed in an extraction cavity, and the extraction cavity filling member 1 was filled in the hole. After the filling, no infection was found in a gum portion, and the member 1 was not dislodged. In addition, since a bone tissue rapidly entered into the porous material 2 embedded in the bone tissue, the porous material 2 was firmly bonded to the bone tissue. Bone absorption in the extraction cavity was prevented to keep the shape of an alveolar ridge.

According to the third embodiment, the extraction cavity filling member 1 constituted by a joint member of the dense material 3 and the porous material 2 is formed of $\beta$-tricalcium phosphate having excellent affinity with a living body, the dense material 3 having the mirrorpolished upper surface 3a which hardly allows bacteria to enter is brought into contact with a soft tissue such as a gum portion, and the porous material 2 which facilitates formation of a bone tissue is brought into contact with a bone tissue. Therefore, a gum portion can be reliably protected from infection. In addition, since the extraction cavity member can be firmly bonded to a bone tissue, the member can be reliably protected from being displaced or dislodged. Furthermore, since the portion to be embedded into a bone tissue of an extraction cavity consists of the porous material 2 which can be comparatively easily cut, the portion can be easily formed into a shape corresponding to the extraction cavity, thereby improving the versatility.

In the above embodiment, $\beta$-tricalcium phosphate is used to form the extraction cavity filling member 1. However, hydroxy apatite may be used to form the member 1.

The extraction cavity filling member shown in FIG. 1 was actually formed by using hydroxy apatite and transplanted in an extraction cavity. As a result, bone absorption in the extraction cavity was prevented to keep the shape of an alveolar ridge. In addition, infection from a soft tissue at an upper portion was prevented, and the extraction cavity filling member was not dislodged. Note that the formation of a bone tissue was slower than that of the above embodiment using $\beta$-tricalcium phosphate.

4th Embodiment

FIG. 2 shows the fourth embodiment of the present invention, in which side and bottom views of an extraction cavity filling member are shown. This extraction cavity filling member 10 is obtained by forming a calcium phosphate compound consisting of a dense material into a shape shown in FIG. 2. Referring to FIG. 2, an upper portion 12 is a dense surface portion to be brought into contact with a gum portion when the member 10 is filled in an extraction cavity. A lower portion 13 is a bone bonding portion to be embedded in a bone tissue of a living body. The surface of the bone bonding portion 13 is roughened, and its distal end is parabolic. Semi-circular pillar-like recess portions 13a to 13d are formed in the circumferential surface of the filling member along its insertion direction.

A method of manufacturing the above extraction cavity filling member 10 will be described below. First, 100 g of a $\beta$-tricalcium phosphate having a particle size of 0.2 $\mu$m or less and a Ca/P molar ratio of 1.50, 20 cc of pure water, and 5 cc of a 10% polyacrylic ammonium salt solution as a deflocculating agent are added and mechanically mixed by a zirconia pot mil for two hours, thereby preparing a slurry. This slurry is injected in a split mold having a desired shape. Note that the split mold used in this embodiment has a parabolic bottom surface and semi-circular pillar-like projections formed along the circumferential surface extending from the bottom surface. The slurry injected in the split mold is dried at room temperature for a long time period. After the slurry is sufficiently dried, it is sintered at a temperature of 1,100° C. for one hour.

A part of the surface of a sintered material is subjected to a sandblasting treatment. That is, a portion (corresponding to the bone bonding portion 13 shown in FIG. 2) to be brought into contact with a bone tissue when the filling member is filled in an extraction cavity is sandblasted by using glass beads at 5 atm for 30 seconds to 7 minutes to obtain a roughened surface. In this manner, the extraction cavity filling member 10 shown in FIG. 2 is obtained.

Extraction cavity filling members 20 and 30 shown in FIGS. 3 and 4 have square-pillar-like recess portions 15a to 15d and triangular pyramidal recess portions 16a to 16h, respectively, in the circumferential surface of a bone bonding portion 3. These extraction cavity filling members are obtained following the same procedures as in the method of manufacturing the extraction cavity filling member 1.

FIG. 5 is a view showing circumferential and bottom surfaces of a comparative extraction cavity filling member for conducting comparative experiments with respect to the extraction cavity filling members 10, 20, and 30 shown in FIGS. 2, 3, and 4, respectively. A portion 41 of the member 40 to be brought into contact with a gum portion when the member is filled in an extraction cavity has a dense surface, and its portion 42 to be embedded in a bone tissue is formed to have a cylindrical portion.

The experiments for comparing the extraction cavity filling members 10, 20, and 30 with the comparative extraction cavity filling member 40 will be described below. Molars of a grown dog were extracted, and the extraction cavity filling members 10, 20, and 30 were filled in the extraction cavities and extracted therefrom after three months. As a result, the members 10, 20, and 30 filled in the extraction cavities of the grown dog were adhered to a bone tissue and strongly fixed. An extraction test was conducted by using the comparative extraction cavity filling member 40 shown in FIG. 5. As a result, the member 40 could be extracted by a smaller force than those required for extracting the members 10, 20, and 30 shown in FIGS. 2, 3, and 4, respectively. As is apparent from these experimental results, the members 10, 20, and 30 adhere to a bone tissue faster and provide better bonding states with a bone than those obtained by the member 40 having the shape as shown in FIG. 5. When embedded portions of the extraction cavity filling members 10, 20, and 30 and the comparative extraction cavity filling member 40 were roentgen-observed, no significant difference was found in alveolar ridge absorption between the members 10, 20, and 30, and the comparative member 40.

According to the fourth embodiment as described above, since the dense surface 12 which hardly allows bacteria to enter is brought into contact with a gum portion, infection due to bacteria from the extraction cavity filling member can be reliably prevented. In addition, the semi-circular pillar-like, square-pillar-like, and triangular pyramidal recess portions 13a to 13d, 15a to 15d, and 16a to 16h, respectively are formed in the portion to be brought into contact with a bone tissue. Therefore, a bone tissue easily adheres to the bone bonding portion 13 to provide a good bonding state with a bone, thereby stably maintaining the extraction cavity filling members 10, 20, and 30. Therefore, the extraction cavity filling members can be protected from being displaced or dislodged.

5th Embodiment

Figures 7, 8:
FIG. 7 is a side view showing a root post.
FIG. 8 is a bottom view showing an extraction cavity filling member in which triangular-pillar-like grooves are formed in a lower fitting hole.

The fifth embodiment allows the extraction cavity filling members 10, 20, and 30 of the fourth embodiment to have a function as an artificial root receiving member. FIG. 6 is a view showing circumferential and bottom surfaces of such an extraction cavity filling member. This extraction cavity filling member 50 is formed into a circular-pillar-like shape and has a dense surface portion 51 to be brought into contact with a gum portion upon extraction cavity filling and a bone bonding portion 52 to be embedded in a bone tissue and having a roughened surface subjected to a sandblasting treatment using glass beads. A shallow cutting guide t for forming an artificial root is formed in the upper end face central portion of the dense surface portion 51. A stepwise abutment tooth support recess 54 is formed around the cutting guide recess 53. FIG. 7 is a side view showing a root post 60 to be applied to the extraction cavity filling member 50. This root post 60 has a hollow portion 61 formed in an axial central portion. Referring to FIG. 7, an abutment tooth 62 is mounted on the upper end portion of the root post 60. A circular-pillar-like lower fitting hole 55 having the same diameter as that of the cutting guide recess 53 is formed concentrically with the cutting guide recess 53. Semi-circular pillar-like grooves 56 for mechanically fitting the root post 60 in the hole 55 are formed in a wall surface 55a which defines the hole 55. In order to mechanically fit the root post 60, triangular-pillar-like grooves 57 may be formed in the wall surface 55a as shown in FIG. 8.

The extraction cavity filling member 50 having the above arrangement was sterilized and transplanted in a molar extraction cavity of a grown dog. After six months from the transplantation, the root post was transplanted in the extraction cavity filling member 50. That is, an epithelium of a gum portion was cut, and the upper end face of the exposed member 50 was cut along lower fitting hole 55 by using a water-activated diamond bur. The root post 60 having the same diameter as that of the lower fitting hole 55 was inserted together with a bonding agent in the hole 55. The abutment tooth 62 was placed in the abutment tooth support recess 54, and was crowned. The state observed after crowning was good.

As described above, according to the fifth embodiment, the extraction cavity filling member 50 has the dense surface portion 51 to be brought into contact with a gum portion and the roughened surface at the bone bonding portion 52 to be embedded in a bone tissue. Therefore, the same effects as in the fourth embodiment can be obtained. In addition, the cutting guide recess 53 having the same diameter as that of the root post 60 and the abutment tooth support recess 54 are formed in the upper end face of the dense surface portion 51 of the member 50, and the lower fitting hole 55 is formed in the bone bonding portion 52 so as to be concentrical with the cutting guide recess 53. Therefore, a hole for transplanting the root post 60 can be easily cut along the cutting guide recess 53. As a result, the extraction cavity filling member can be used as an artificial root receiving member.

What is claimed is:

1. An extraction cavity filling member used to fill an extraction cavity formed by extraction of a tooth, to prevent alveolar ridge lowering, said filling member comprising:
    a first end portion formed of a dense material such as to prevent bacteria from entering said extraction cavity and placed in contact with a gum portion located in the vicinity of said extraction cavity; and
    a second end portion formed of a porous material such as to promote formation of a bone tissue of a living body located in said extraction cavity, said second end portion being adapted to be brought into contact with said bone tissue;
    wherein said first end portion and said second end portion are formed of β-tricalcium phosphate having affinity with a living body and ability to firmly bond to a bone tissue, and are formed into a unitary body.

2. The member according to claim 1, wherein said second end portion has at least one recess portion.

3. The member according to claim 1, wherein said second end portion has a surface in which at least one recess portion is formed.

4. The member according to claim 3, wherein said recess portion is a groove.

5. The member according to claim 1, wherein said first end portion has an end face in which a cutting guide hole having a predetermined diameter is formed, and said second end portion has a root post transplanting hole having the same diameter as that of said guide hole and formed concentrically with said guide hole.

6. The member according to claim 5, wherein said cutting guide hole has a step portion for supporting an abutment tooth.

7. The member according to claim 5, wherein said root post transplanting hole has a wall surface in which a plurality of recess portions are formed.

8. The member according to claim 1, wherein the Ca/P molar ratio of said $\beta$-tricalcium phosphate is 1.50.

9. The member according to claim 8, wherein the porous material has a porosity of about 50% and has pores with a pore diameter of 100 $\mu$m.

* * * * *